(12) United States Patent
Nelson et al.

(10) Patent No.: US 8,617,164 B2
(45) Date of Patent: Dec. 31, 2013

(54) SURGICAL RASPING SYSTEMS AND METHODS

(75) Inventors: Keith J. Nelson, Logan, UT (US); Nathan D. Hansen, Hyde Park, UT (US); M. Mary Sinnott, Logan, UT (US); Joseph Q. Marietta, Hyde Park, UT (US)

(73) Assignees: IMDS Corporation, Providence, UT (US); Keith S. Nelson, Logan, UT (US)

( * ) Notice: Subject to any disclaimer, the term of this patent is extended or adjusted under 35 U.S.C. 154(b) by 464 days.

(21) Appl. No.: 12/765,451

(22) Filed: Apr. 22, 2010

(65) Prior Publication Data
US 2011/0071527 A1 Mar. 24, 2011

Related U.S. Application Data

(60) Provisional application No. 61/245,487, filed on Sep. 24, 2009.

(51) Int. Cl.
*A61B 17/00* (2006.01)
*A61B 17/32* (2006.01)

(52) U.S. Cl.
USPC ............................................ 606/85; 606/171

(58) Field of Classification Search
USPC .......... 606/79–85, 171, 176, 177; 81/52, 429; 30/392–394; 83/698.11, 699.21, 83/698.31, 697, 628; 403/359.1, 395.5, 403/395.6

See application file for complete search history.

(56) References Cited

U.S. PATENT DOCUMENTS

| | | | |
|---|---|---|---|
| 3,596,525 A | 8/1971 | Niesz |
| 3,884,238 A | 5/1975 | O'Malley |
| 4,108,182 A | 8/1978 | Hartman |
| 4,210,146 A | 7/1980 | Banko |
| 4,246,902 A | 1/1981 | Martinez |
| 4,314,560 A | 2/1982 | Helfgott |
| 4,530,357 A | 7/1985 | Pawlaski |
| 4,589,414 A | 5/1986 | Yoshida |
| 4,700,702 A | 10/1987 | Nilsson |
| 4,727,941 A | 3/1988 | Fulton |

(Continued)

FOREIGN PATENT DOCUMENTS

| | | |
|---|---|---|
| WO | WO9913789 | 3/1999 |
| WO | WO03053278 | 7/2003 |

(Continued)

OTHER PUBLICATIONS http://global.smith-nephew.com/us/DYINICS_ARTHOSCOPIC Smith & Nephew Dyonics & Powermax Elite.

(Continued)

*Primary Examiner* — Andrew Yang
*Assistant Examiner* — Diana S Jones
(74) *Attorney, Agent, or Firm* — G. Jo Hays; James Larson; James M. Pinkston

(57) ABSTRACT

A surgical rasping system functional in multiple orthopedic applications, including but not limited to shoulder, knee, hip, wrist, ankle, spinal, or other joint procedures. The system comprises a rasping head which may be low profile and offer a flat cutting/rasping surface, and is configured to be driven by an attached hub that translates a rotational movement into a reciprocating motion. Suction for removal of bone fragments or other tissues is provided through an opening spaced apart from or adjacent to the rasping surface.

14 Claims, 20 Drawing Sheets

(56) References Cited

U.S. PATENT DOCUMENTS

| | | | |
|---|---|---|---|
| 4,728,319 | A | 3/1988 | Masch |
| 4,936,845 | A | 6/1990 | Stevens |
| 5,152,744 | A * | 10/1992 | Krause et al. .................. 604/22 |
| 5,185,934 | A | 2/1993 | Tilman |
| 5,285,816 | A | 2/1994 | Herlihy |
| 5,364,395 | A | 11/1994 | West |
| 5,387,215 | A | 2/1995 | Fisher |
| 5,403,276 | A | 4/1995 | Schechter |
| 5,411,513 | A | 5/1995 | Ireland |
| 5,437,630 | A | 8/1995 | Daniel |
| 5,490,860 | A | 2/1996 | Middle |
| 5,540,693 | A * | 7/1996 | Fisher ........................... 606/79 |
| 5,593,415 | A | 1/1997 | Adrian |
| 5,632,759 | A | 5/1997 | Rexroth |
| 5,643,304 | A | 7/1997 | Schechter |
| 5,669,876 | A | 9/1997 | Schechter |
| 5,685,840 | A | 11/1997 | Schechter |
| 5,707,374 | A | 1/1998 | Schmidt |
| 5,810,860 | A | 9/1998 | Adrian |
| 5,814,049 | A | 9/1998 | Pratt |
| 5,817,050 | A | 10/1998 | Klein |
| 5,833,643 | A | 11/1998 | Ross |
| 5,925,055 | A | 7/1999 | Adrian |
| 5,957,881 | A | 9/1999 | Peters |
| 6,042,593 | A | 3/2000 | Storz |
| 6,048,345 | A | 4/2000 | Berke |
| 6,083,228 | A | 7/2000 | Michelson |
| 6,368,324 | B1 | 4/2002 | Dinger |
| 6,451,022 | B2 | 9/2002 | Dinger |
| 6,537,280 | B2 | 3/2003 | Dinger |
| 6,595,996 | B2 | 7/2003 | Dinger |
| 6,610,066 | B2 | 8/2003 | Dinger |
| 6,635,060 | B2 | 10/2003 | Hanson |
| 6,751,875 | B2 | 6/2004 | Jones |
| 7,070,604 | B1 | 7/2006 | Garito |
| 7,226,459 | B2 | 6/2007 | Cesarini |
| 7,390,330 | B2 | 6/2008 | Harp |
| 7,510,563 | B2 | 3/2009 | Cesarini |
| 7,569,057 | B2 | 8/2009 | Liu |
| 7,666,186 | B2 | 2/2010 | Harp |
| 7,837,700 | B2 | 11/2010 | Harp |
| 7,883,476 | B2 | 2/2011 | Miller |
| 2001/0037114 | A1 | 11/2001 | Dinger |
| 2004/0049217 | A1 | 3/2004 | Ross |
| 2005/0065529 | A1 * | 3/2005 | Liu et al. ....................... 606/79 |
| 2006/0026117 | A1 | 2/2006 | Raman |
| 2006/0058732 | A1 | 3/2006 | Harp |
| 2006/0079919 | A1 | 4/2006 | Harp |
| 2006/0129159 | A1 | 6/2006 | Lee |
| 2006/0161189 | A1 | 7/2006 | Harp |
| 2006/0200153 | A1 | 9/2006 | Harp |
| 2006/0200154 | A1 | 9/2006 | Harp |
| 2006/0200155 | A1 | 9/2006 | Harp |
| 2006/0259055 | A1 | 11/2006 | Thorne |
| 2007/0021766 | A1 | 1/2007 | Belagali |
| 2007/0208353 | A1 | 9/2007 | Shadduck |
| 2008/0021487 | A1 * | 1/2008 | Heisler ......................... 606/170 |
| 2008/0047143 | A1 | 2/2008 | Quan |
| 2008/0058820 | A1 | 3/2008 | Harp |
| 2008/0103446 | A1 | 5/2008 | Salstrom et al. |
| 2009/0177202 | A1 * | 7/2009 | May et al. ....................... 606/79 |

FOREIGN PATENT DOCUMENTS

| | | |
|---|---|---|
| WO | WO2004002331 | 1/2004 |
| WO | WO2004028351 | 4/2004 |
| WO | WO2005009213 | 2/2005 |
| WO | WO2005020826 | 3/2005 |
| WO | WO2006047598 | 5/2006 |
| WO | WO2009005458 | 1/2009 |

OTHER PUBLICATIONS http://www.depuymitekfms.com/products/shavers FMS (DePuy MItek, Inc) Shavers and Burrs.
https://www.arthrex.com/innovations/top-left.cfm?adid=27 Arthrex CoolCut, Sabertooth and Excaliber, Clearcut (Burrs).
http://www.conmed.com/products_power_react.php Conmed React, Great White, Gator, Full Radius Resector, Cuda, Tiger (Burrs).
http://www.mdmmedical.com/shaver_blades_burs.tml MDM Medical; Shavers and Burrs (UK).
http://www.stryker.com/ens/products/Endoscopy/Arthroscopy?AccessoriesDisposables/CuttersandBurs/index.htm Stryker; Cutters and Burrs.
http://www.comeg.de/eng/pages/produkte/med_arthroskopie.htm Comeg; Shavers.
http://syedsurgical.com/rhinologyl.htm SYED Surgical: Rasps.
http://www.microaire.com/kommerce_productdata.
aspx?class=117 MicroAire; Rasps.
Arthrex; Product Brochure, 2008 pp. 1-2.
Arthronet; Product Brochure, Cat_D_R00 / Seite 1-15.
ConMed; Product Brochure, CBR 0030 Rev.4 Jun. 2008 p. 1.
ConMed; Product Brochure, CCA 9029 Rev.1 Jun. 2007 pp. 1-194.
ConMed; Product Brochure, CCA 9030 Dec. 2006 pp. 1-102.
Eberle; Product Insert, IND#080204B p. 1.
Fiegert Endotech; Product Catalog, E11/07 p. ACC 31.
Gimmi Endoscopic Technology; Product Catalog pp. 1-64 170/01 MKMC.
ConMed Linvatec; ReAct Shaver, Product Brochure, Sep. 2008 CBR 0038 pp. 1-2.
Arthroskopie Arthrocopy; REMA shaver Blades, Product Brochure.
http:www.therhinoplastycenter.com/poweredrasp.html, May 20, 2009 pp. 1-4, The Rhinoplasty.
Vokurka, J.; Shaver (Micro Debridor) in Otorhinolarynoglogy, International Congress Series 1240 (2003) 1411-1415.
Tekno; Product Catalog, pp. 1-24.
Arthrex.com; Myarthrex Product Brochures 2008; LR06551.

* cited by examiner

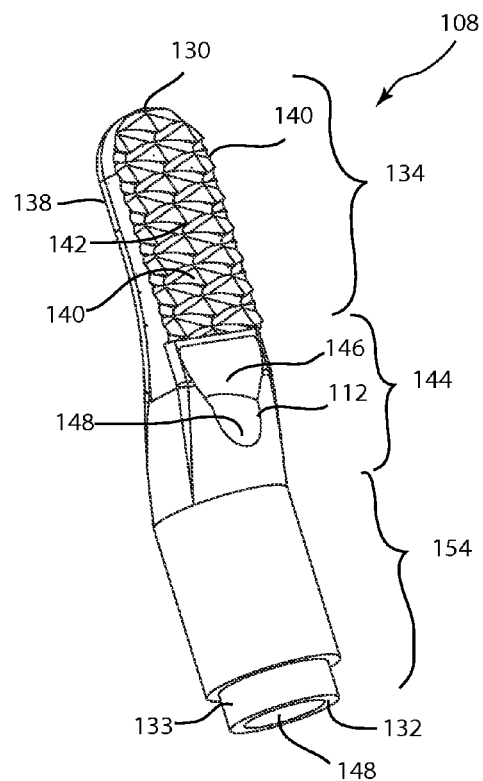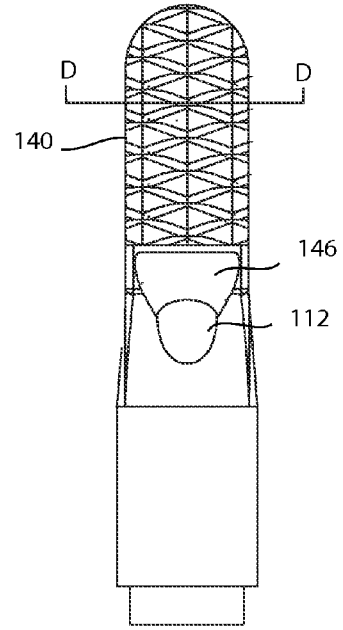
Fig. 3A          Fig. 3B
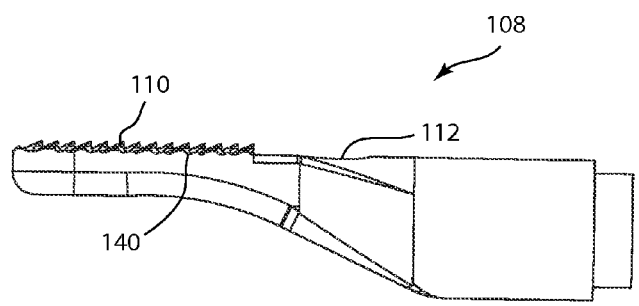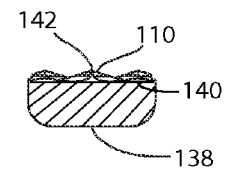
Fig. 3C          Fig. 3D

SURGICAL RASPING SYSTEMS AND METHODS

CROSS-REFERENCE TO RELATED APPLICATIONS

This application claims the benefit of the following:
pending U.S. Provisional Patent Application No. 61/245, 487, filed Sep. 24, 2009, and is entitled SURGICAL RASPING SYSTEM.

The above-identified document is incorporated herein by reference.

FIELD OF THE INVENTION

This invention relates to surgical tissue removal devices by which anatomical tissues may be cut and removed from a joint or other operative site. Specifically, this invention relates to rasping instruments having reciprocating motion and suction.

BACKGROUND OF THE INVENTION

Surgical procedures including subacromial decompression, arthroscopic resection of the acromioclavicular joint (also known as the Mumford procedure), and anterior cruciate ligament reconstruction involving notch plasty, may all necessitate removal of osteophytes. Other conditions such as chondromalacia and osteochondritis dissecans may call for removal of osteophytes or chondrocytes. It is known to use shavers and burrs having rotational cutting surfaces to remove these hard tissues. However, the round cutting surface of a shaver or burr system is not advantageous to creating or preparing a flat surface. The forces applied while using a rotational round cutting surface tend to pull the cutting end to either side by a moment force pivoting on the hand making precise control difficult. Working in confined spaces may exacerbate these issues, as adjacent soft tissues may easily be grabbed by a rotating cutting surface. Therefore, the need exists for an instrument with a reciprocating, flat cutting surface to provide a surgeon with greater control over the instrument and enhanced ability to create/prepare a flat tissue surface, especially in confined areas.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 3A in an enlarged isometric view of a rasp head of the rasping system of FIG. 1A; FIG. 3B is a front view of the rasp head of FIG. 3A; FIG. 3C is a side view of the rasp head of FIG. 3C; FIG. 3D is a cross-sectional view of the rasp head of FIG. 3A taken along section line D-D;

DETAILED DESCRIPTION OF THE PREFERRED EMBODIMENTS

The present invention relates to tissue removal devices and methods by which body tissues may be cut and removed during surgery. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The present invention provides a rasping system that is shaped such that it is functional in multiple orthopedic surgery applications, including but not limited to shoulder, knee, hip, wrist, ankle, spinal, or other joint procedures. The system comprises a rasping head which may be low profile and offer a flat cutting/rasping surface, and is configured to be driven by an attached hub that will translate a rotational movement into a reciprocating motion. Suction for removal of bone fragments or other tissues may be provided through an opening in or adjacent the rasping head.

This device provides an alternative method of removing hard tissue to the currently used shavers and burrs that offer a rotational cutting surface. By applying a reciprocating flat cutting surface the surgeon has greater control over the instrument and is better able to create/prepare a flat surface. The reciprocating force of the rasp applies resisting pressure to the surgeons hand in the axial direction with the hand, making control much easier. Increased control will result in a decrease in injury to the surrounding soft tissue. The rasp also has a lower profile than many of the existing shaver systems allowing access to tight joints without damaging surrounding tissues. The teeth of the rasp may be positioned such that the cut material will be pulled towards the suction pathway to more efficiently remove debris from the surgical site, thus decreasing the duration of a procedure.

Figure 1A:
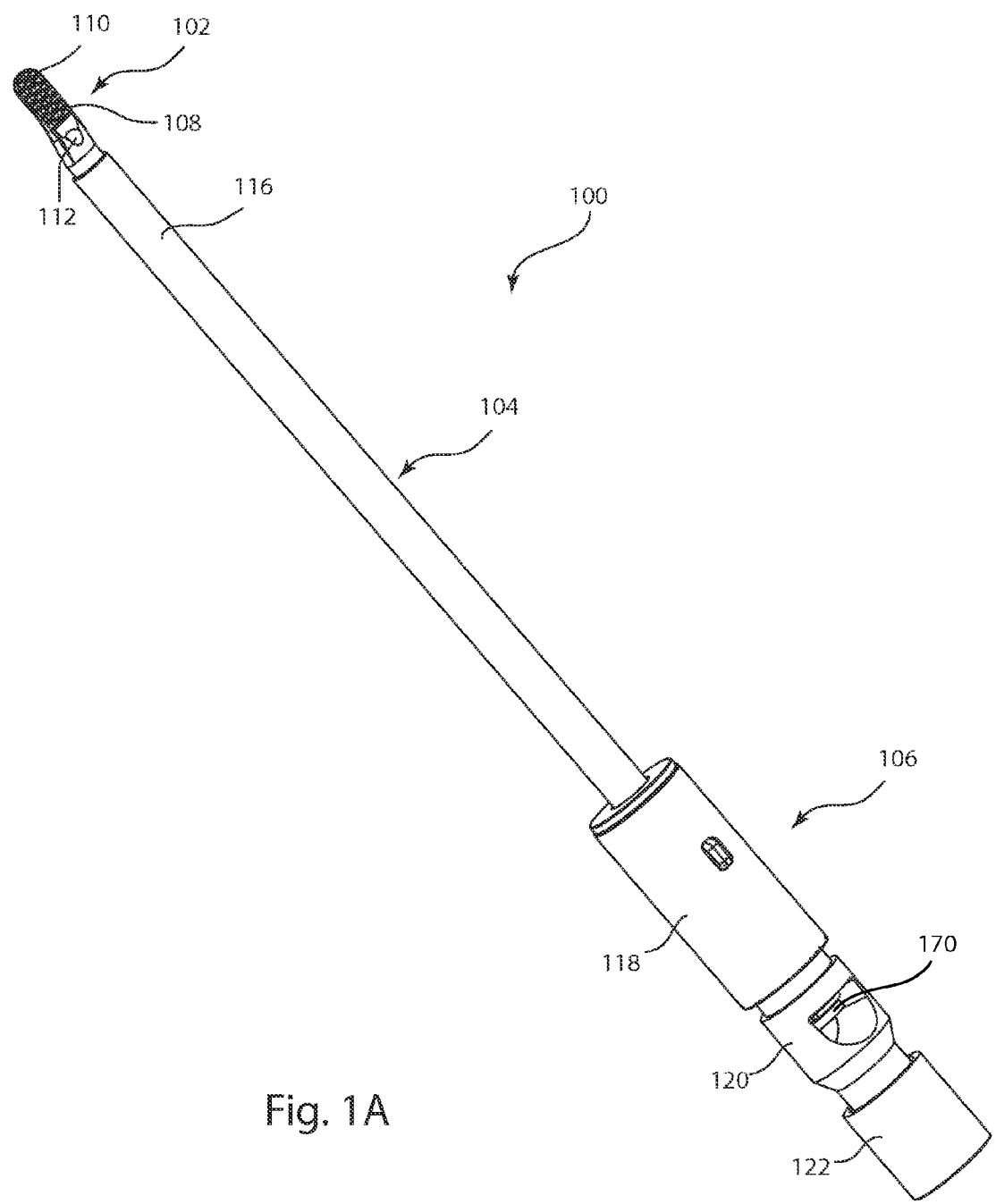
FIG. 1A is an isometric view of a reciprocating rasping system.

Referring to FIG. 1A, rasp system 100 is shown in an isometric view. Rasp system 100 comprises head portion 102, shaft portion 104, and handle portion 106. Head portion 102 comprises rasp head 108, which includes a plurality of teeth 110 or cutting edges which may cut anatomical tissues when drawn along the tissue surface. A suction opening 112 is located on the head portion 102, and may be disposed between the teeth and the shaft portion. The shaft portion 104 comprises inner shaft 114 (not visible in FIG. 1A) which extends proximally from the rasp head 108 and is received in the handle portion 106. The inner shaft 114 extends through an optional outer sleeve 116 which is joined to the handle portion 106. At its proximal end, inner shaft 114 is received within a shaft key 170 (not visible in FIG. 1A).

Handle portion 106 includes an outer housing 118, a driving hub 120, and a spring collet 122 which houses a spring 250 (not visible in FIG. 1). Outer housing 118 comprises a cam surface (not visible in FIG. 1) which is complementarily shaped to a cam follower surface on driving hub 120. When handle portion 106 is engaged in a powered rotary handpiece and power is supplied, hub 120 rotates, and the cam and cam follower surfaces provide a motion conversion mechanism which converts the rotary motion of the hub to axial reciprocal motion of the inner shaft 114 and attached head 108. Rasp system 100 is connectable via spring collet 122 to a powered handpiece, to provide rotary power to the rasp system, and to provide suction. Suitable handpieces include the Linvatec Advantage Shaver (Ref D9824) brand powered rotary handpiece or another similar system known in the art.

Figure 1B:
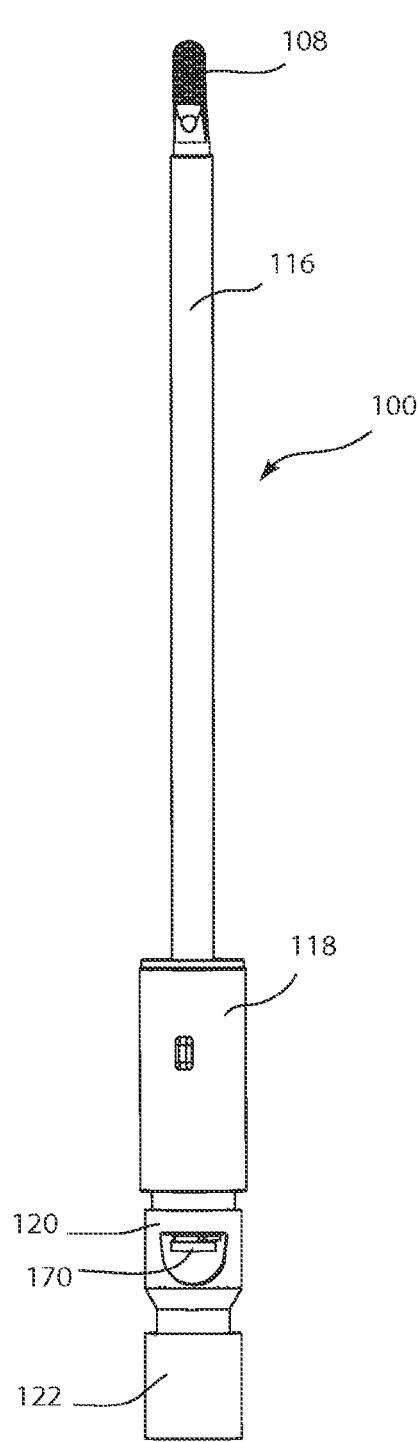
FIG. 1B is a front view of the rasping system of FIG. 1A in a retracted configuration.
Figure 1C:
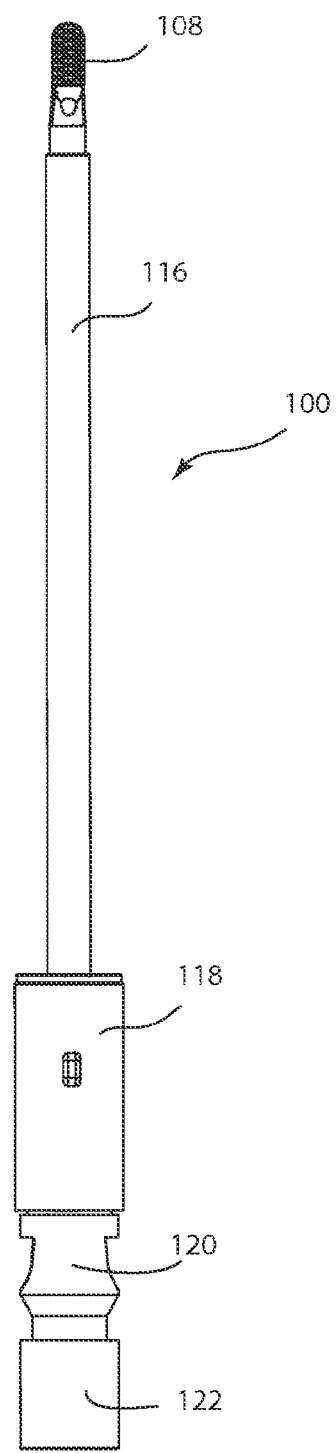
FIG. 1C is a front view of the rasping system of FIG. 1A in an extended configuration.

FIG. 1B illustrates rasp system 100 in a retracted configuration. In this configuration, the shaft key 170, inner shaft 114 (not visible; within outer sleeve 116) and rasp head 108 have been pulled by interaction of the cam and cam follower surfaces to a proximal position. FIG. 1C illustrates rasp system 100 in an extended configuration. In this configuration, driving hub 120 has rotated relative to the outer housing 120; and the shaft key, inner shaft 114 and rasp head 108 have been reciprocally translated to a distal position by the spring bias of spring 250. It is appreciated that an alternate embodiment of the invention may include a curved inner shaft and, optionally, a curved outer sleeve. In the curved embodiment the rasp head may be angled relative to the inner shaft, and the outer sleeve may be sized to allow free reciprocation of the inner shaft.

Figure 2:
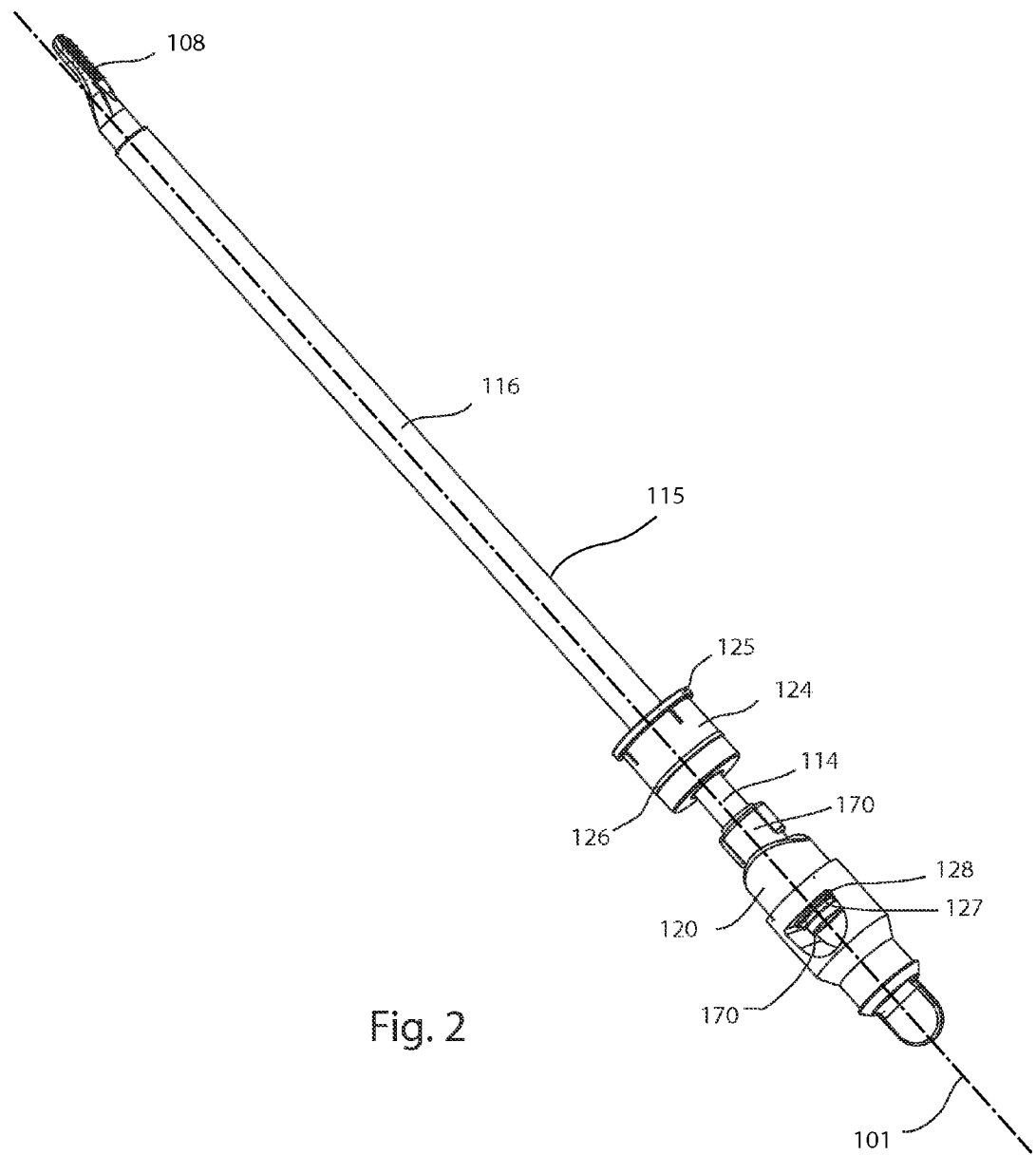
FIG. 2 is an isometric view of the rasping system of FIG. 1A with an outer housing and collet removed, and a longitudinal axis of the rasping system.

FIG. 2 illustrates rasp system 100 minus the outer housing 118 and spring collet 122. Outer sleeve 116 is joined to plug 124. Plug 124 comprises a rim 125 and a protruding ring 126. When received within the outer housing 118 as in FIG. 1, ring 126 may provide a snap connection with a groove feature within outer housing 118, and rim 125 may seat against a distal end of the outer housing. Once joined with the outer housing 118, plug 124 and outer sleeve do not translate or rotate relative to the outer housing. The outer sleeve 116 provides protection to surrounding tissues when rasp system 100 is used; outer sleeve 116 does not rotate or reciprocate, yet allows reciprocal movement of inner shaft 114 within. Space between the inner shaft 114 and the outer sleeve 116 may optionally be lubricated. Together, the rasp head 108, inner shaft 114 and shaft key 170 comprise a tissue removal member 115.

Proximal to the plug 124, the inner shaft 114 is received in the shaft key 170 and is non-movable relative to the shaft key. A portion of shaft key 170 is received within a portion of hub 120, which is rotatable about the shaft key. A snap ring 127 is received in a groove formed at the proximal end of the shaft key, and retains the shaft key 170 within the hub 120 while still allowing the hub 120 to rotate about the shaft key. A washer 128 is positioned around the shaft key 170 between the snap ring 127 and the hub 120. The system 100 comprises a longitudinal axis 101 about which the hub 120 rotates, and along which the tissue removal member 115 is reciprocally translated.

Referring to FIGS. 3A through 3D, several views of rasp head 108 are shown. Rasp head 108 comprises a distal end 130, and a proximal end 132, and further comprises a working portion 134, a head transition portion 144 and a head shaft portion 154. The working portion 134 comprises a first side 136 which may be also be known as a front side, and a second, or back side 138 opposite the first side. A tissue removal surface 140 is disposed on the first side 136, although it is appreciated that in alternate embodiments, the tissue removal surface may be disposed on the back side, or on both the front and back sides. The tissue removal surface 140, may be flat as in FIGS. 3A-3D, or in other embodiments may be concave or convex. The plurality of teeth 110 populates the tissue removal surface, each tooth having a cutting portion 142. The cutting portion 142 may be a point as seen in the teeth depicted in FIGS. 2A-2D, but in other embodiments the cutting portion may be an edge, or a combination of one or more edges and a point. The teeth may be distributed individually; in even ranks or rows; or in alternate ranks or rows. In alternative embodiments of the cutting head, the number, size, and distribution of the teeth may vary to provide a variety of tissue cutting surfaces suitable for different tissue removal procedures. The cutting portions 142 may be uni-directionally oriented as in FIGS. 3A-3D, meaning that all of the teeth point the same direction. Advantageously, the teeth may be pointed toward the suction opening 112, thus facilitating efficient movement of cut debris into the suction opening. Another feature of uni-directional teeth is that the teeth may only cut into tissue when the rasp head is moved in one direction; for example if the teeth are pointed proximally, cutting will occur when the rasp head is translated proximally.

The transition portion 144 extends between the working portion and the head shaft portion, and may be angled relative to the working and/or head shaft portions. Proximal to and spaced apart from the tissue removal surface, the suction opening 112 provides a distal opening to a suction pathway. A fan-like scoop portion 146 adjacent the suction opening 112 may funnel excised tissue toward the suction opening. A head suction bore 148 extends proximally from the suction opening 112, forming a portion of the suction pathway.

The head shaft portion 154 extends from the transition portion 144 to the proximal end 132 of the rasp head 108. At the proximal end 132, a fitting or connection feature 133 allows for joining of the rasp head 108 to the inner shaft 114. The head suction bore 148 terminates at the proximal end 132, but the suction pathway continues through the hollow inner shaft 114. The rasp head 108 may be removably joined to the inner shaft via a press fit or mechanical fit, or may be permanently joined via a weld or other permanent connection.

Figures 4A, 4B:
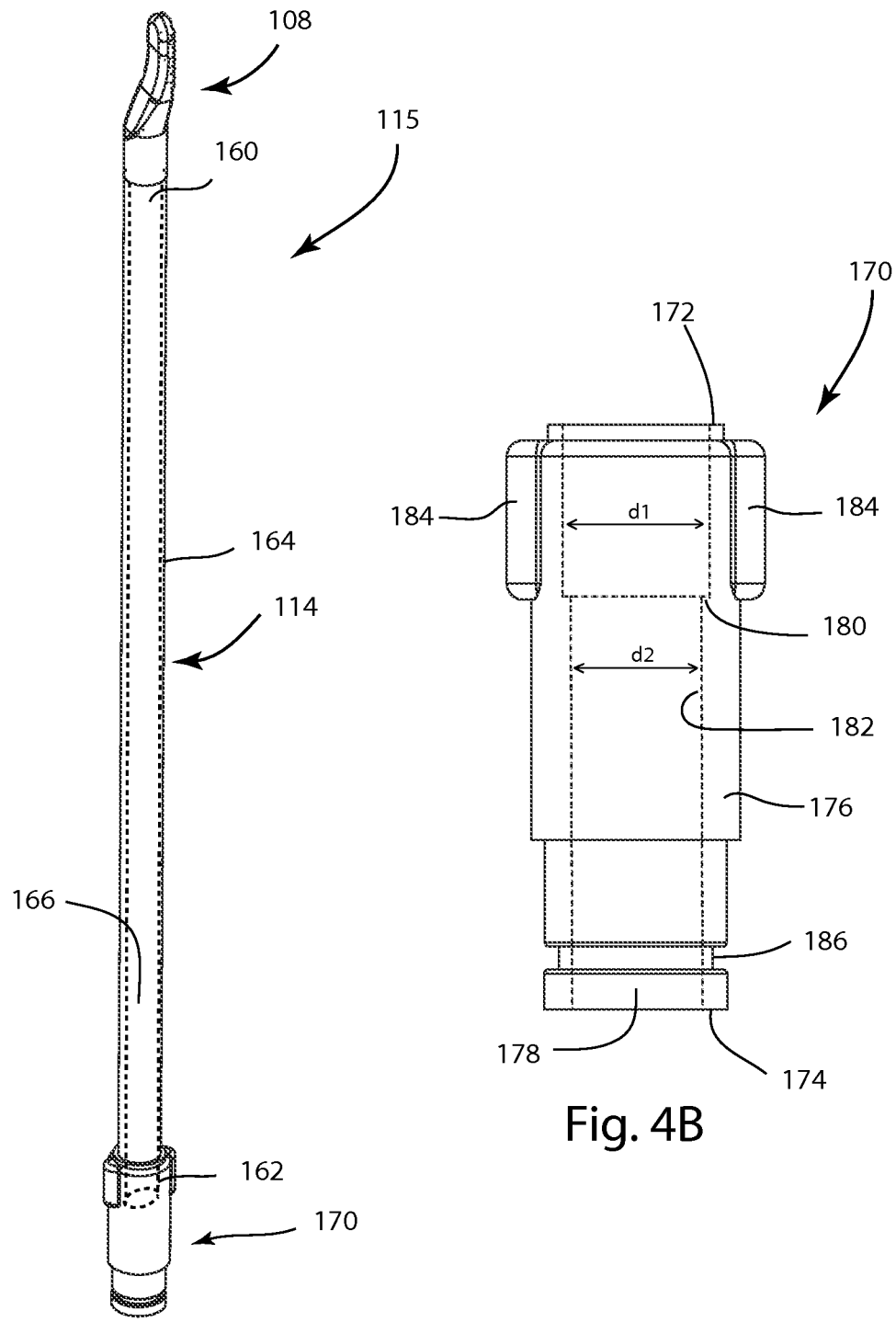
FIG. 4A is a iso-side view of a tissue removal member of the rasping system of FIG. 1A.
FIG. 4B is an enlarged side view of a shaft key of the tissue removal member of FIG. 4A.

FIG. 4A illustrates the rasp head 108, inner shaft 114, and a shaft key 170, which together comprise the tissue removal member 115. The inner shaft 114 comprises a tubular member having a distal end 160, a proximal end 162 and an inner shaft body 164 extending therebetween. The inner shaft body defines an inner shaft bore 166, indicated by dashed lines, extending from the distal end to the proximal end, forming a portion of the suction pathway. The proximal end 162 of the inner shaft is received in the shaft key 170. Inner shaft 114 may be glued, welded, bonded, press fit or otherwise permanently joined to shaft key 170, so that no movement including translation or rotation between inner shaft 114 and shaft key 170 is allowed. Inner shaft 114 may be monolithically formed with shaft key 170.

Referring to FIG. 4B, shaft key 170 comprises a distal end 172, a proximal end 174, and generally cylindrical key body 176 extending therebetween. A key bore 178 (indicated by dashed lines) extends the length of the shaft key, and forms a portion of the suction pathway. At its distal end, the key bore has a first diameter d1 dimensioned to receive the proximal end of the inner shaft 114. Proximal to a shoulder 180 formed in an inner wall 182 of the key body 176, the key bore has a second diameter d2. Two individual wings 184 protrude from the key body 176, opposite from one another near the distal end 172. The wings 184 are shaped to be received in recesses formed within the outer housing, preventing rotation of the tissue removal member when the hub is rotated. It is appreciated that in other embodiments of the invention, the number and placement of the wings 184 may vary, or the wings may be formed on the outer housing, to be received in recesses formed on the shaft key 170. Toward the proximal end 174 of the shaft key 170, an annular groove 186 is formed on the outside of the key body 176. The groove 186 is shaped to receive snap ring 127. The suction pathway comprises the continuous pathway formed by head suction bore 148, inner shaft bore 166 and key bore 178.

Outer housing 118 is illustrated in FIGS. 5A through 5D. The tissue removal member 115 is receivable in the outer housing, while the outer housing is shaped to be received in a powered handpiece. Outer housing 118 is generally cylindrical and comprises a distal end 190, a proximal end 192 and an outer housing body 194 extending therebetween. A tab 196 protrudes exteriorly from the outer housing body, and is shaped to be received in a groove formed in a powered handpiece, to both properly align the rasp system 100 within the handpiece and prohibit rotation of the outer housing 118 relative to the handpiece.

Figure 5A:
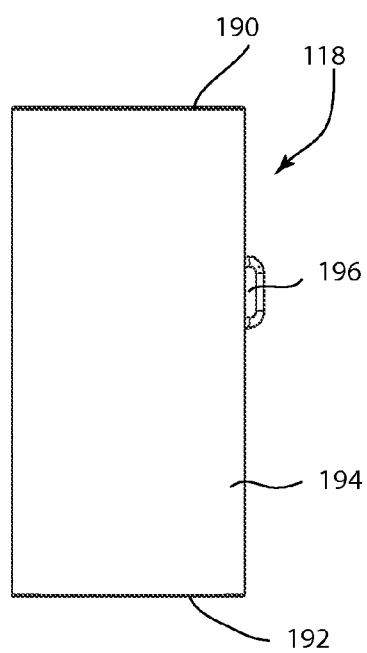
FIG. 5A is a side view of an outer housing of the rasping system of FIG. 1A.
Figure 5B:
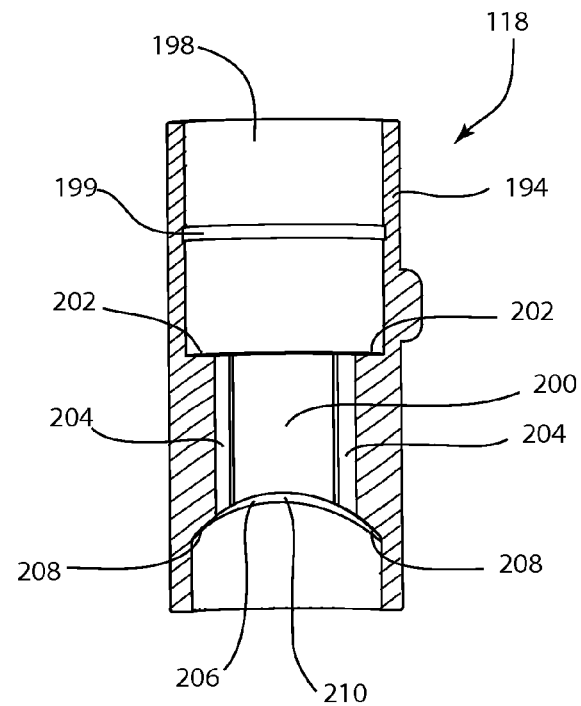
FIG. 5B is cross-sectional view of the outer housing of FIG. 5A, taken along line B-B of FIG. 5C.
Figure 5C:
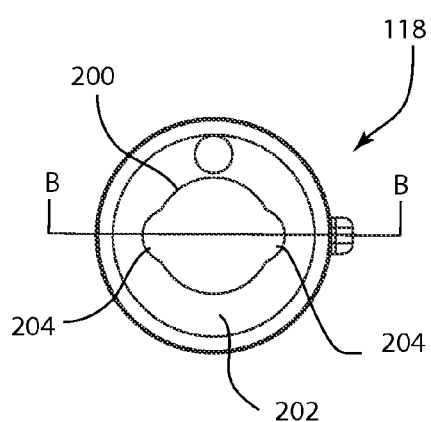
FIG. 5C is a top end view of the outer housing of FIG. 5A.

FIG. 5B is a longitudinal cross-sectional view of the housing, taken along line B in FIG. 5C. Extending longitudinally through the housing is housing bore 198. Toward the distal end of the housing, bore 198 is shaped to receive the generally cylindrical plug 124 (not shown) which in turn receives the outer sleeve 116. An annular inner groove 199 is shaped to fit around the ring 126 on the outer surface of the plug. An annular shoulder 202 is formed in the inner wall of the housing body 194. A keyway, or key portion 200 of the housing bore 198 is constricted, and shaped to receive a portion of the shaft key 170. Two recesses 204 in the key portion 200 are shaped to complementarily fit the wings 184 of the shaft key 170. When the shaft key 170 is received in the key portion 200 of the housing 118, the complementary fit of the wings 184 in the recesses 204 prohibits rotation of the shaft key 170, and thus tissue removal member 115, relative to the outer housing 118, but allows proximal-distal/distal-proximal translation of the shaft key 170 relative to the outer housing.

Figure 5D:
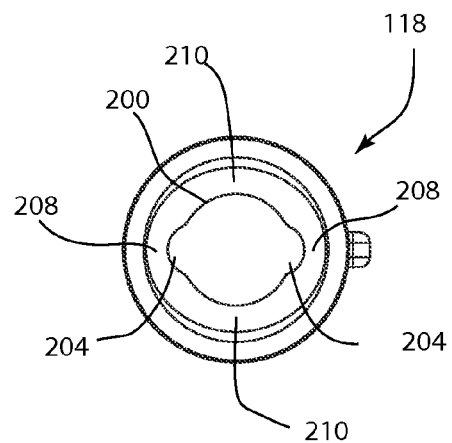
FIG. 5D is a bottom end view of the outer housing of FIG. 5A.

Referring to FIG. 5D, a bottom end view shows an undulating, annular cam surface 206 formed in the inner wall of the housing body 194. The annular cam surface 206 comprises two lobes 208, formed as two portions which protrude proximally, parallel to the longitudinal axis, on opposite sides of the bore 198 from one another. At the lobes 208, cam surface 206 slopes proximally from its outer diameter to its inner diameter. The lobes 208 are evenly interspersed with two hollows 210, such that, when viewed from the side, the annular cam surface 206 undulates evenly between two low points at the lobes 208, and two high points at the hollows 210.

Figure 6A:
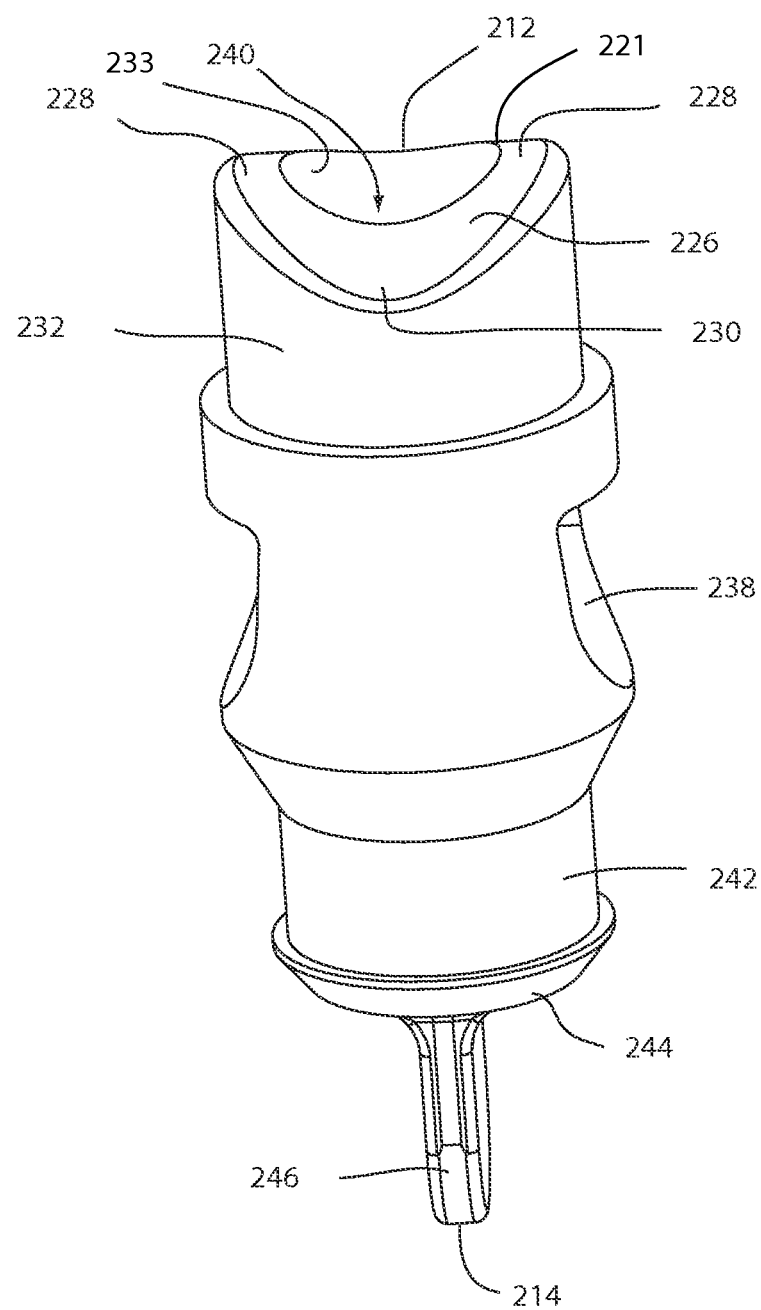
FIG. 6A is an isometric view of a first side of a driving hub of the rasping system of FIG. 1A.
Figure 6B:
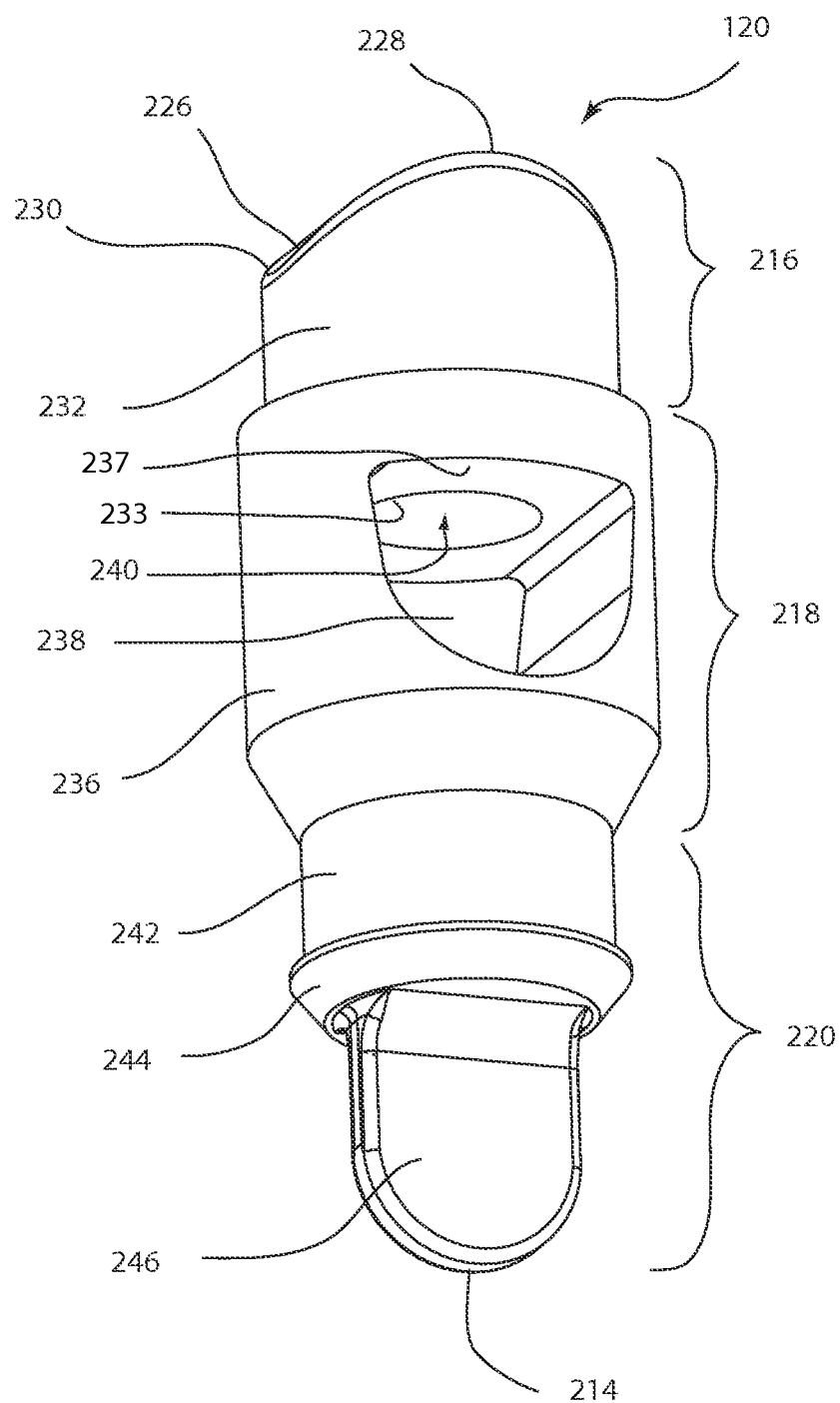
FIG. 6B is an isometric view of a second side of a driving hub of the rasping system of FIG. 1A.

The driving hub 120 is illustrated in FIGS. 6A and 6B. The hub 120 extends longitudinally between a distal end 212 and a proximal end 214. The hub 120 comprises three portions: a distal cam portion 216, an intermediate portion 218, and a proximal driving portion 220. At the distal end 212, the hub terminates in a distal end face 221 having a cam follower surface 226 which is shaped complementarily to the cam surface 206. The cam follower surface comprises two follower lobes 228 interspersed with two follower hollows 230. At the follower hollows 230, cam follower surface 226 slopes proximally from its outer diameter to its inner diameter. The follower lobes 228 are evenly interspersed with the follower hollows 230, such that, when viewed from the side, the cam follower surface 226 undulates evenly between two low points at the hollows 230, and two high points at the lobes 228. The distal cam portion 216 is circumscribed by an annular outer wall 232. A driving hub bore 240, lined by an annular inner wall 233, extends longitudinally through the distal cam portion 216.

The intermediate portion 218 of the hub 120 comprises an intermediate body 236, through which an aperture 238 extends transversely. The driving hub bore 240 continues longitudinally from the distal cam portion 216 and terminates at a proximal hub face 237, in communication with the aperture 238. The driving hub bore 240 forms the proximal portion of the suction pathway, which terminates with the aperture.

The driving portion 220 of the driving hub 120 provides a connection feature for connection to a powered handpiece. The driving portion 220 comprises a smooth, cylindrical hub body 242 which terminates at an annular flange 244. The flange 244 forms a lip extending exteriorly from the hub body. Proximal to the hub body and flange, a plate-like driving tab 246 projects longitudinally, and transversely across the diameter of the hub body. The driving tab 246 is shaped to be coupled with a driver in the powered handpiece, to provide rotational motion to the driving hub. It is appreciated that in other embodiments of the invention, the connection to the powered handpiece may take other forms, including but not limited to a square, star, cross, X-shape, H-shape, or other form compatible with the handpiece.

Figure 7A:
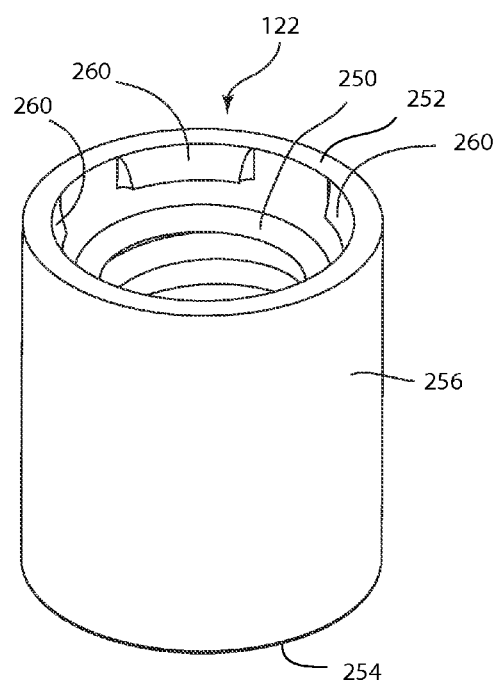
FIG. 7A is an isometric view of a spring collet and spring of the rasping system of FIG. 1A.
Figure 7B:
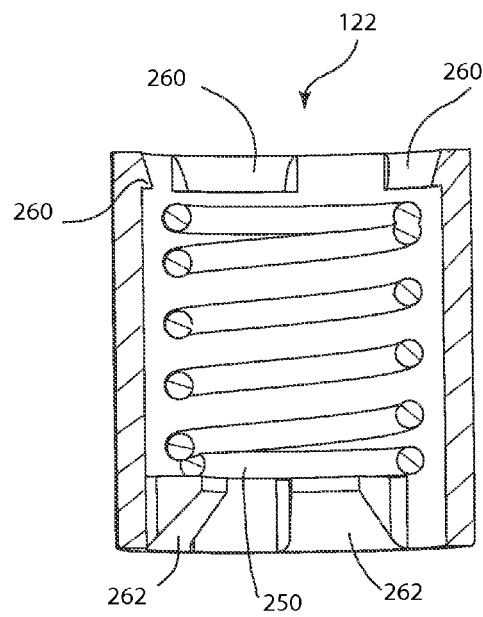
FIG. 7B is cross-sectional view of the spring collet and spring along section line B-B of FIG. 7C.
Figure 7C:
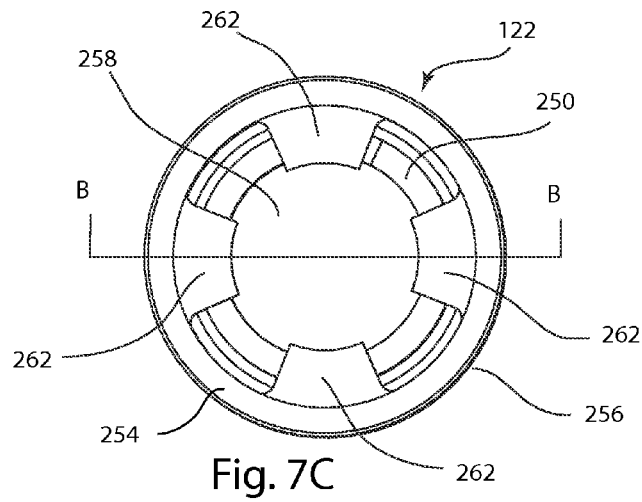
FIG. 7C is a bottom end view of the spring collet and spring of FIG. 7A.

Referring to FIGS. 7A through 7C, the spring collet 122 and a spring 250 are illustrated. Spring collet 122 is generally cylindrical and tubular in form, comprising a distal end 252, a proximal end 254, and a tubular collet body 256 extending therebetween. A collet bore 258 is defined and surrounded by the collet body 256. Adjacent the distal end 252, a plurality of distal stops 260 formed on the collet body 256 protrude inward into the collet bore 258. When the collet 122 is coupled with the driving hub 120, distal stops 260 cooperate with flange 244 to prevent the collet from becoming uncoupled yet allow rotation of the hub relative to the collet. Adjacent the proximal end 254, a plurality of proximal stops 262 formed on the collet body 256 protrude inward into the collet bore 258. As seen in FIG. 7B, the proximal stops may be larger than the distal stops, projecting farther into the collet bore. The proximal stops 262 prevent the spring 250 from escaping proximally out of the spring collet 122 and provide a platform against which the spring may be compressed. When coupled in collet 122 with driving hub 120, spring 250 is biased to push the driving hub 120 distally unless otherwise acted upon.

Figure 8:
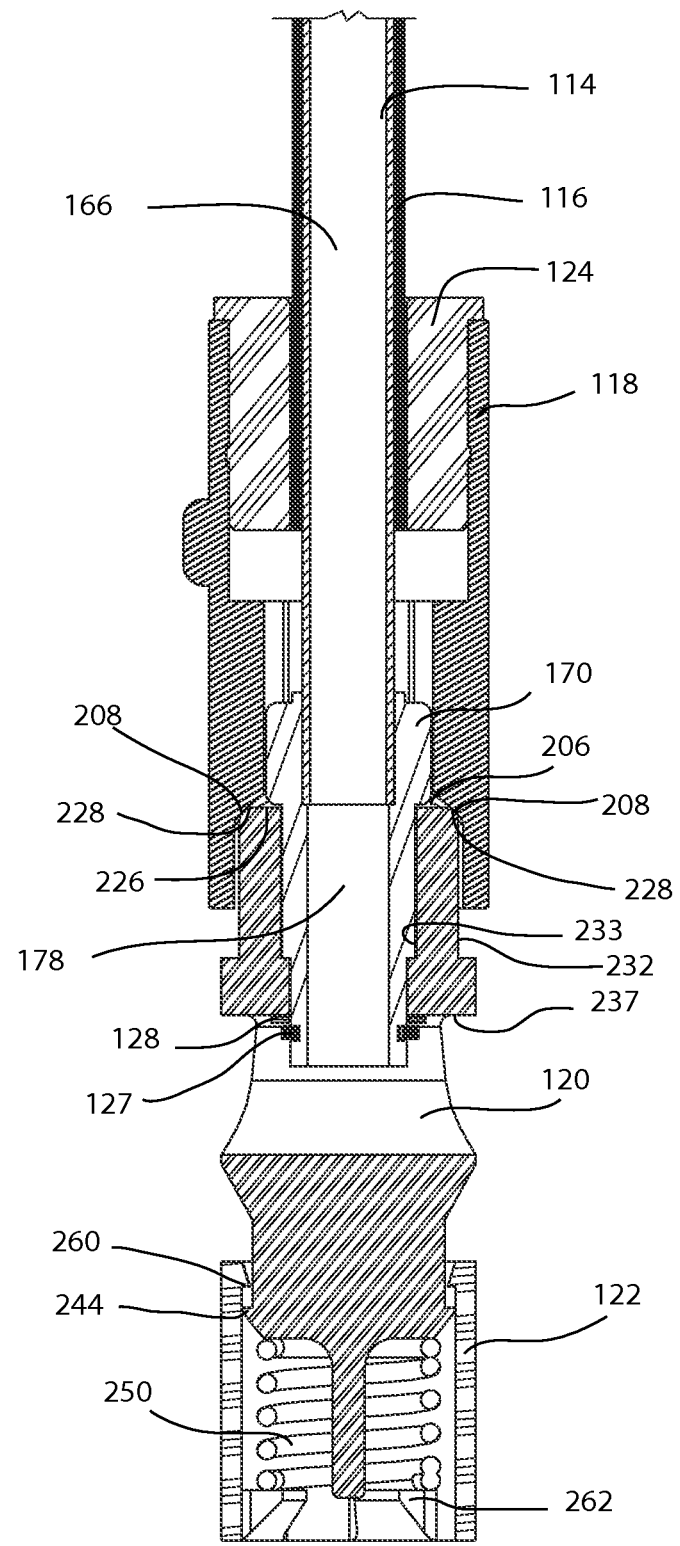
FIG. 8 is a longitudinal cross-sectional view of a handle portion and a segment of a shaft portion of the rasping system of FIG. 1A in the retracted position.
Figure 9:
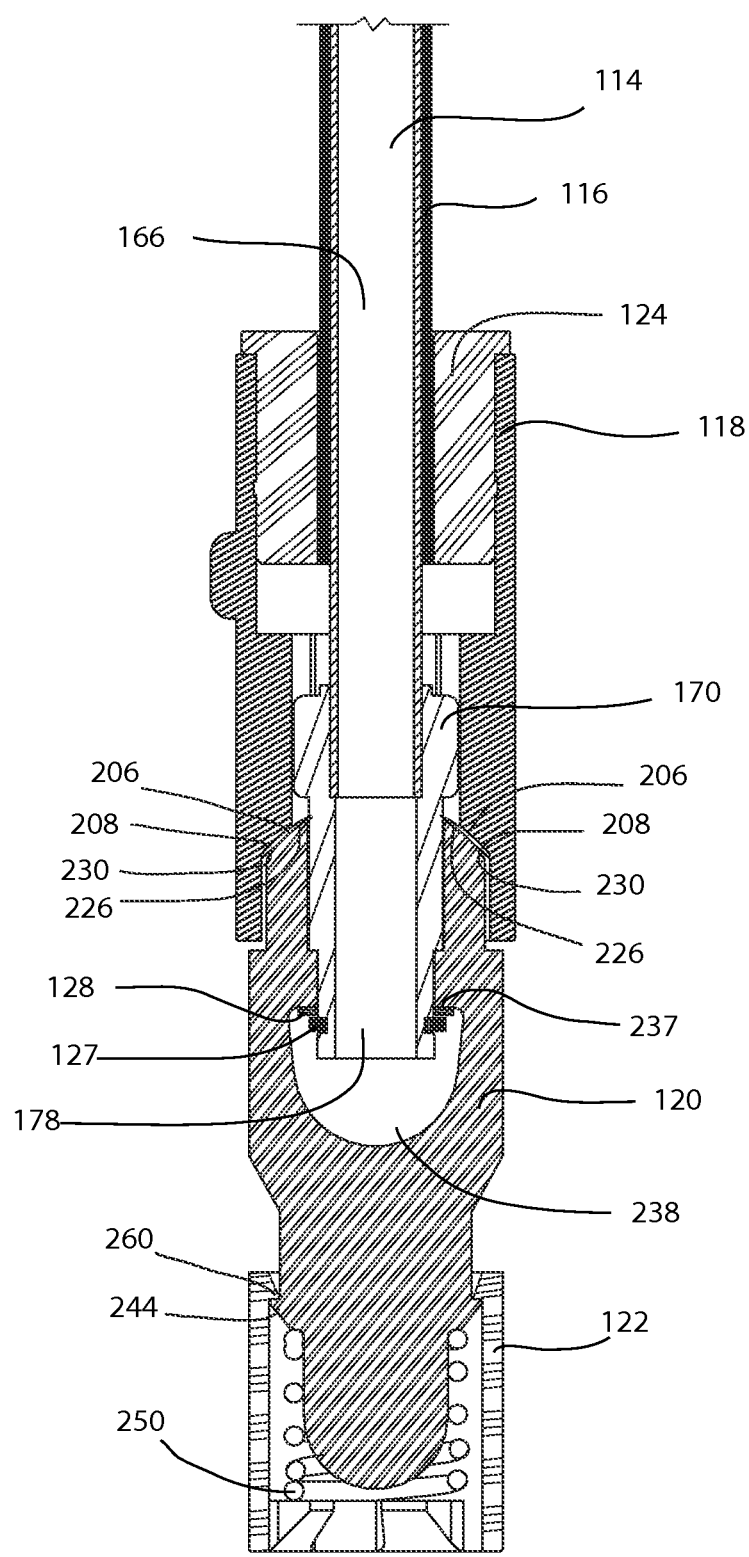
FIG. 9 is a longitudinal cross-sectional view of a handle portion and a segment of a shaft portion of the rasping system of FIG. 1A in the extended position.

FIGS. 8 and 9 provide cross-sectional views of the handle portion and a segment of the shaft portion of rasp system 100. FIG. 8 shows the rasp system 100 in a retracted configuration, in which the tissue removal member 115 comprising shaft key 170, inner shaft 114 and rasp head 108 is in a first position relative to the outer housing 118. FIG. 9 shows the rasp system 100 in an extended configuration, in which the tissue removal member 115 is in a second position relative to the outer housing 118, the second position distal to the first position. When the rasp system 100 is connected to the powered handpiece and power is supplied, hub 120 is rotated, and the interaction of the cam and cam follower surfaces and the bias of the spring convert the rotary motion of the hub to reciprocal motion of the tissue removal member between the extended and retracted configurations.

As set forth previously, inner shaft 114 is joined with shaft key 170; and shaft key 170 is received within housing 118 such that the wings 184 fit in recesses 204, allowing axial translation of shaft key 170 relative to the outer housing 118 but prohibiting rotation of shaft key 170. A proximal portion of shaft key 170 is received within the driving hub bore 240, which is rotatable relative to the shaft key 170 and the outer housing 118. More specifically, the inner wall 233 slidably rotates about the shaft key 170 while the outer wall 232 slidably rotates relative to the housing 118. The cam surface 206 of the outer housing 118 is positioned immediately adjacent the complementary cam follower surface 226 of the driving hub 120. The cam surface 206 of the outer housing 118 is distal to the proximal end of the tissue removal member 115.

A motion conversion mechanism, which may also be called a motion mechanism, is provided by the outer housing including its cam surface and the hub including its cam follower surface. In extended configuration, hub 120 is positioned such that cam follower surface 226 is flush against cam surface 206, with hollows 230 on follower cam surface 226 complementarily fitting against the lobes 208 of cam surface 206. In the retracted configuration, the driving hub 120 is rotated relative to the outer housing 118 such that the lobes 228 on follower cam surface push against the lobes 208 of cam surface 206, thus forcing driving hub 120 proximally, or downward, relative to the outer housing 118. As hub 120 moves proximally, shaft key 170, inner shaft 114 and rasp head 108 are pulled proximally with the hub, but they do not rotate. Proximal hub face 237 rotatably bears against washer 128, which in turn bears against split ring 127, to pull the tissue removal member 115 proximally. As hub 120 continues to rotate, spring 250 pushes distally to axially translate hub 120 back to the extended position, carrying with it shaft key 170, inner shaft 114 and rasp head 108. In the embodiment depicted in FIGS. 8 and 9, cam surface 206 and cam follower surface 226 each have two lobes and two hollows, so that with one full rotation of hub 120, tissue removal member 115 is twice axially reciprocated. In an alternate embodiment, the cam and cam follower surfaces may have more than two lobes and hollows, so that one rotation of the hub may result in multiple reciprocations. In another alternate embodiment, the cam and cam follower surfaces may each have only one lobe and one hollow, resulting in a single reciprocation per revolution. It is appreciated that while the lobes and hollows depicted herein are rounded, however in other embodiments the lobes and/or hollows may be pointed or sharply angular.

As set forth previously, rasp head 108 comprises uni-directionally oriented teeth, which are oriented proximally toward the suction opening 112. Thus, as tissue removal member 115 reciprocates distally and proximally, the teeth cut into any adjacent tissue as the tissue removal member moves proximally. This proximal cutting action may aid in moving cut tissue debris toward the suction opening. Reciprocation of the flat tissue removal surface 115 against the tissue allows for creation or preparation of a flat surface on the tissue.

Figure 10:
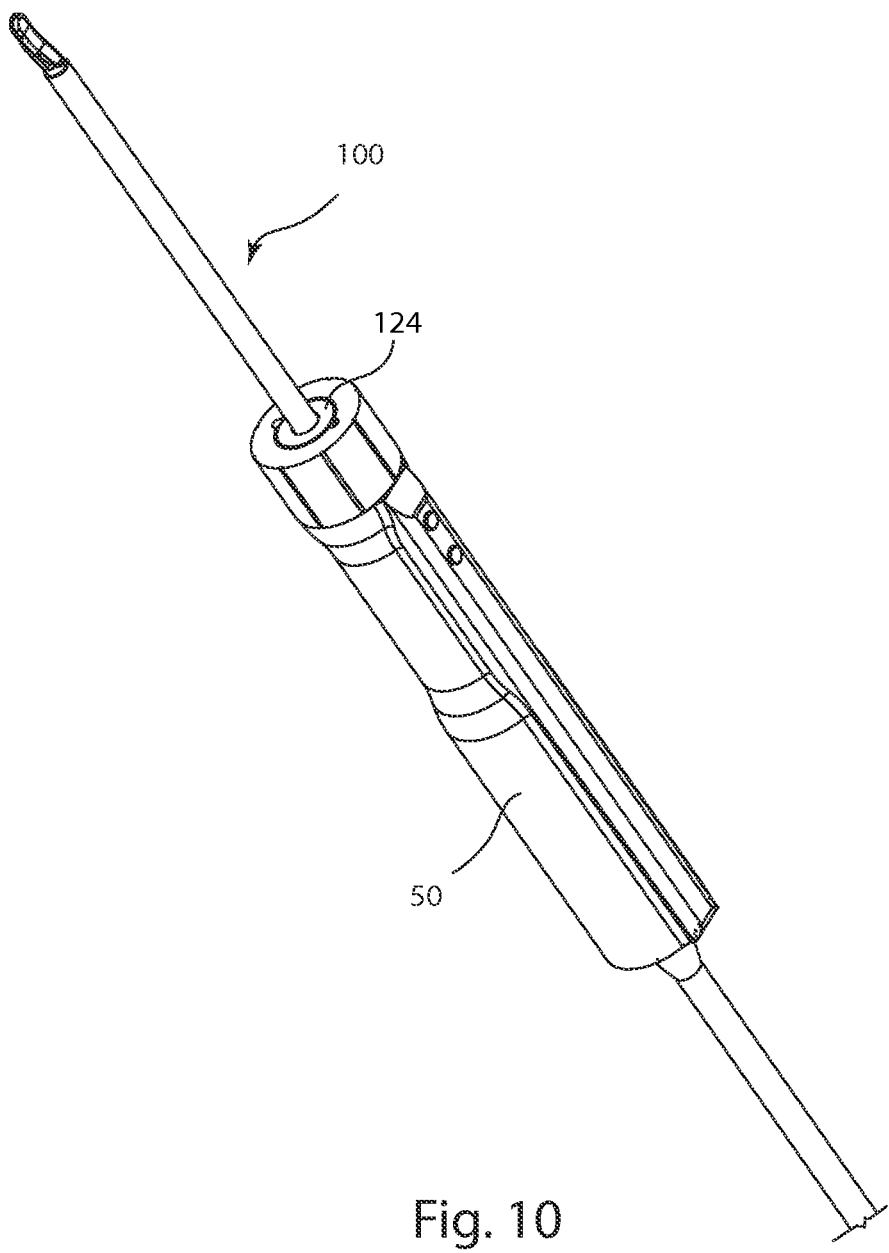
FIG. 10 is an isometric view of the rasping system of FIG. 1A coupled in an exemplary powered handpiece.

FIG. 10 illustrates rasp system 100 engaged in an exemplary powered rotary handpiece 50. Powered rotary handpiece 50 may be a handpiece known in the art, and provides rotary power and suction to rasp system 100. When the rasp system 100 is engaged in the handpiece, the handle portion 106 is surrounded by the handpiece as in FIG. 10, so that no rotating parts are exposed and so that debris pulled through the suction pathway is captured in the handpiece.

FIGS. 11A through 18B set forth alternate embodiments of the rasp head. It is appreciated that alternate embodiments of the rasp system may include any one of the rasp heads disclosed herein, and may include mixed and matched features of the various rasp heads.

Figure 11A:
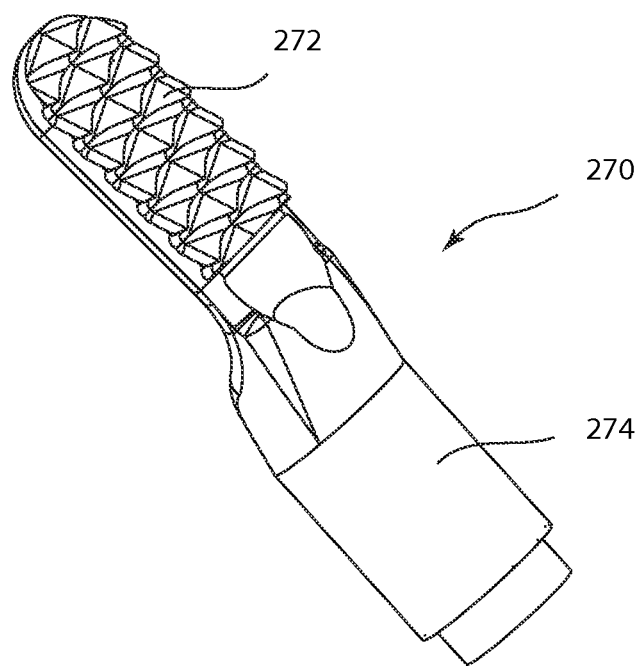
FIG. 11A is an isometric view of an alternate embodiment of a rasp head, a tissue removal portion angled relative to the remainder of the rasp head.
Figure 11B:
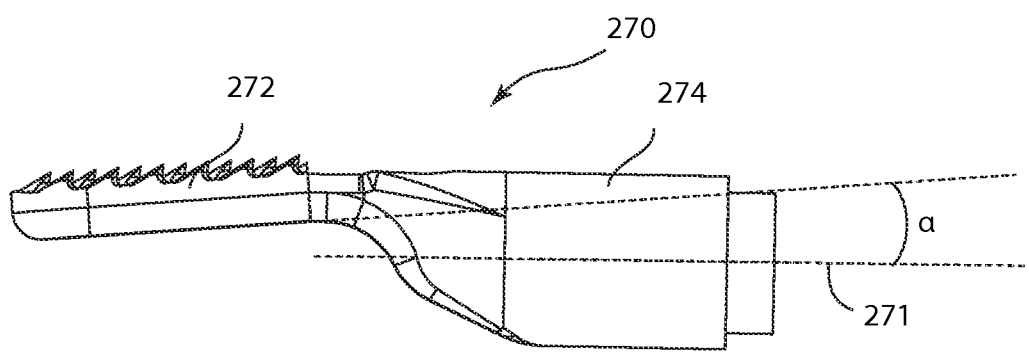
FIG. 11B is a side view of the rasp head of FIG. 11A.

FIGS. 11A and 11B depict a rasp head 270 comprising an angled working portion 272. The working portion 272 is tilted at angle α relative to a longitudinal axis 271 of a head shaft portion 274. Angle α may range from 1 to 10 degrees. More specifically, angle α may range from 3 to 7 degrees. Yet more specifically, angle α may be 5 degrees.

Figure 12A:
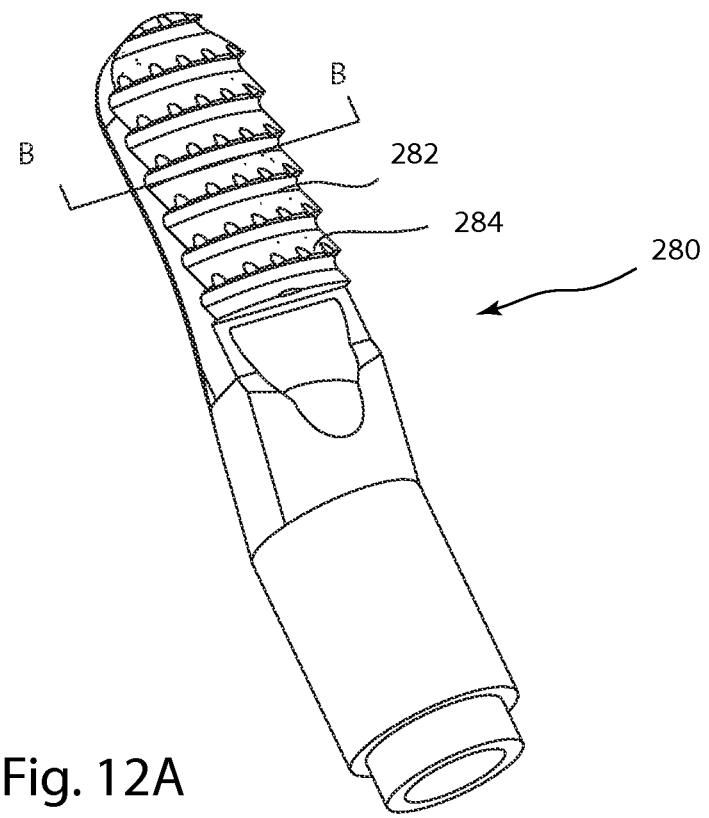
FIG. 12A is an isometric view of an alternate embodiment of a rasp head comprising a convex tissue removal surface.
Figure 12B:
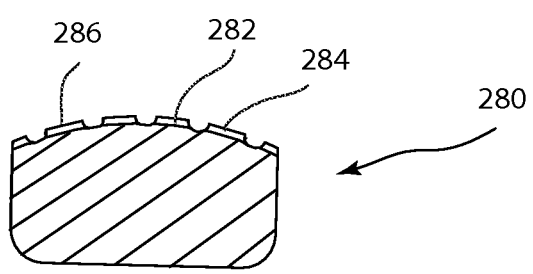
FIG. 12B is a cross-sectional view of the rasp head of FIG. 12A taken along line B-B.

FIGS. 12A and 12B depict a rasp head 280 comprising a convex tissue removal surface 282 from which teeth 284 project. The teeth may comprise straight or curved cutting edges 286; that is the cutting edges 286 may also be convexly curved.

Figure 13A:
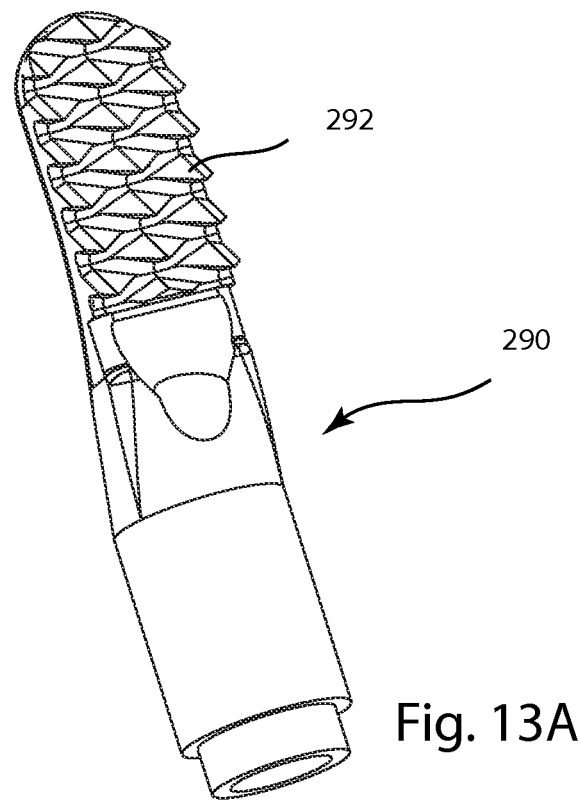
FIG. 13A is an isometric view of an alternate embodiment of a rasp head comprising elongated rasping teeth.
Figure 13B:
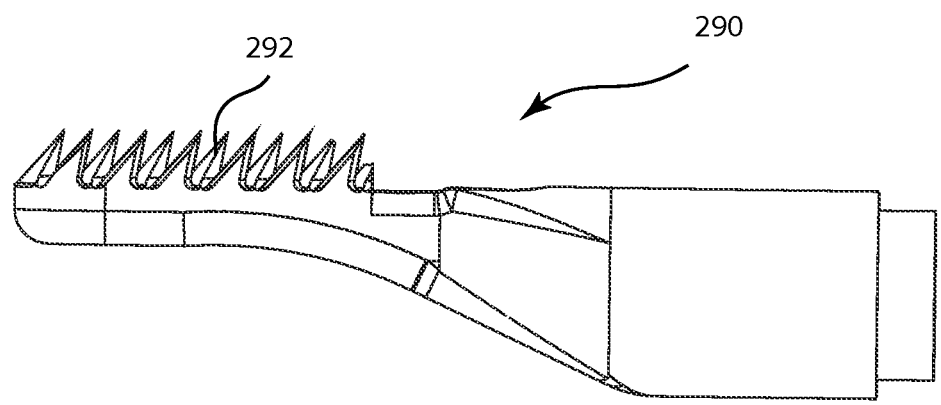
FIG. 13B is a side view of the rasp head of FIG. 13A.

FIGS. 13A and 13B depict a rasp head 290 comprising long teeth 292. The teeth 292 may be longer than teeth in other embodiments and may be advantageous for cutting through relatively softer materials.

Figure 14A:
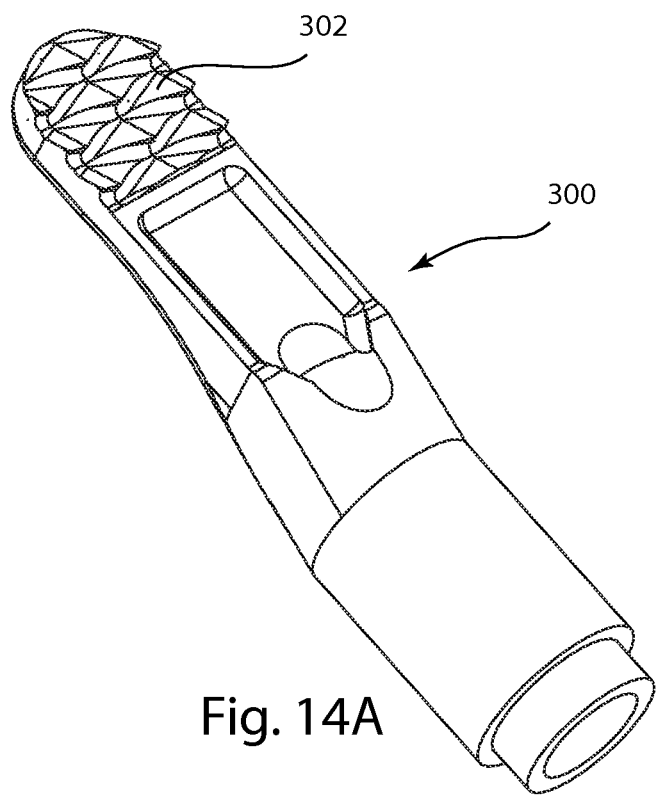
FIG. 14A is an isometric view of an alternate embodiment of a rasp head comprising a reduced tissue removal surface.
Figure 14B:
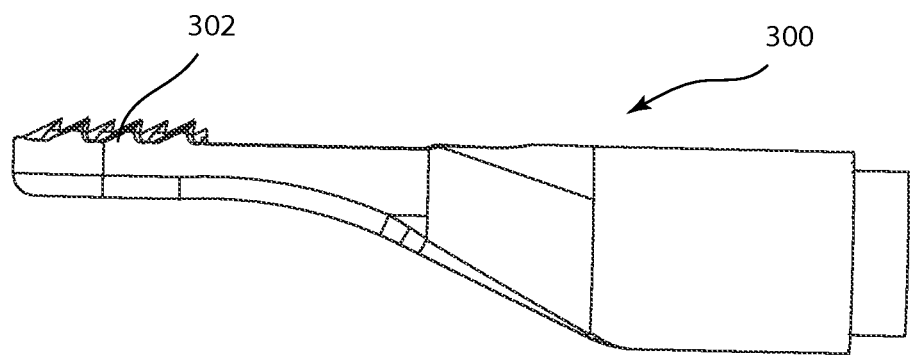
FIG. 14B is a side view of the rasp head of FIG. 14A.

FIGS. 14A and 14B depict a rasp head 300 comprising a relatively smaller tissue removal surface 302. This rasp head may be advantageous for accessing smaller and/or more confined areas such as the wrist joint, and for minimizing contact with tissues adjacent the area targeted for tissue removal. It is appreciated that in alternate embodiments, a smaller tissue removal surface may take the form of a longer but narrower tissue removal surface.

Figure 15A:
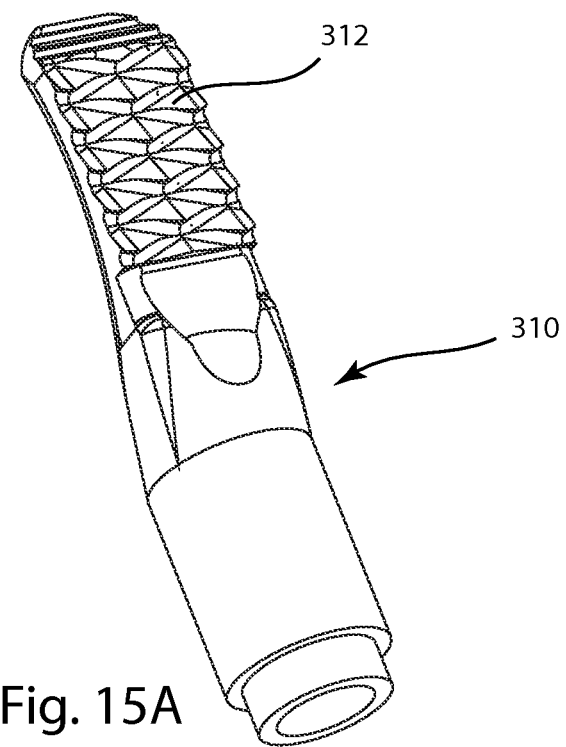
FIG. 15A is an isometric view of an alternate embodiment of a rasp head comprising a crescent-shaped tissue removal surface.
Figure 15B:
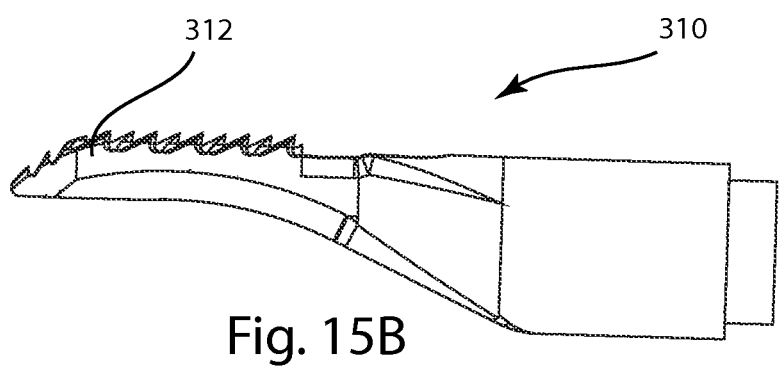
FIG. 15B is a side view of the rasp head of FIG. 15A.

FIGS. 15A and 15B depict a rasp head 310 comprising a curved or crescent-shaped tissue removal surface 312. Tissue removal surface 312 may be convexly curved longitudinally, or both longitudinally and transversely.

Figure 16A:
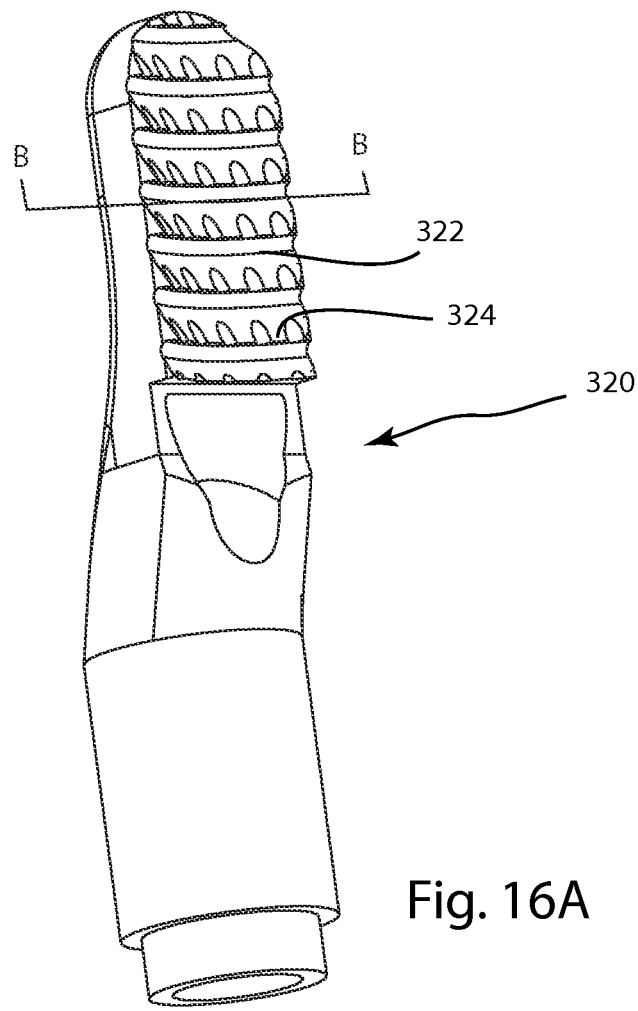
FIG. 16A is an isometric view of an alternate embodiment of a rasp head comprising a concave removal surface.
Figure 16B:
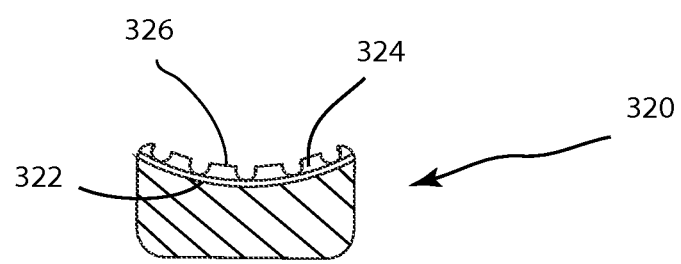
FIG. 16B is a side view of the rasp head of FIG. 16A.

FIGS. 16A and 16B depict a rasp head 320 comprising a concave tissue removal surface 322 from which teeth 324 project. The teeth may comprise straight or curved cutting edges 326; that is the cutting edges 326 may also be concavely curved.

Figure 17A:
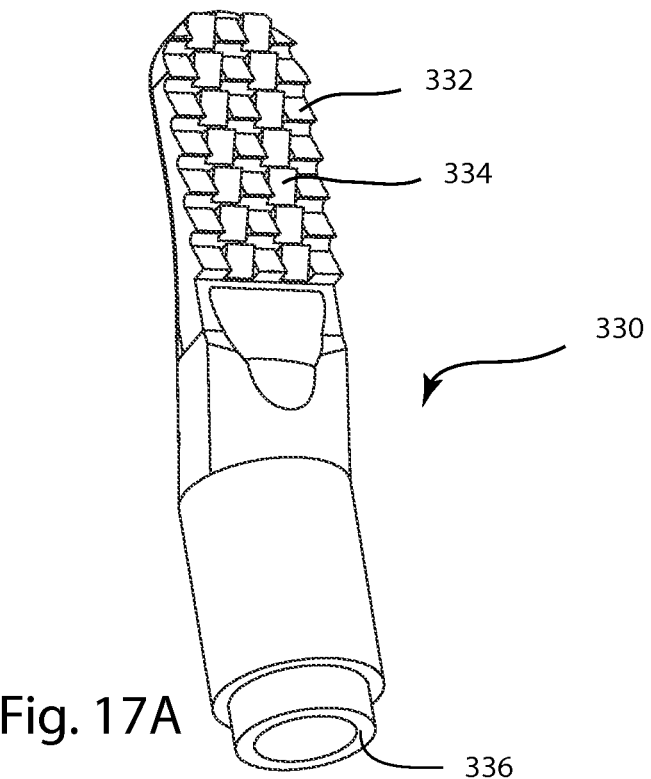
FIG. 17A is an isometric view of an alternate embodiment of a rasp head comprising bi-directional rasping teeth.
Figure 17B:
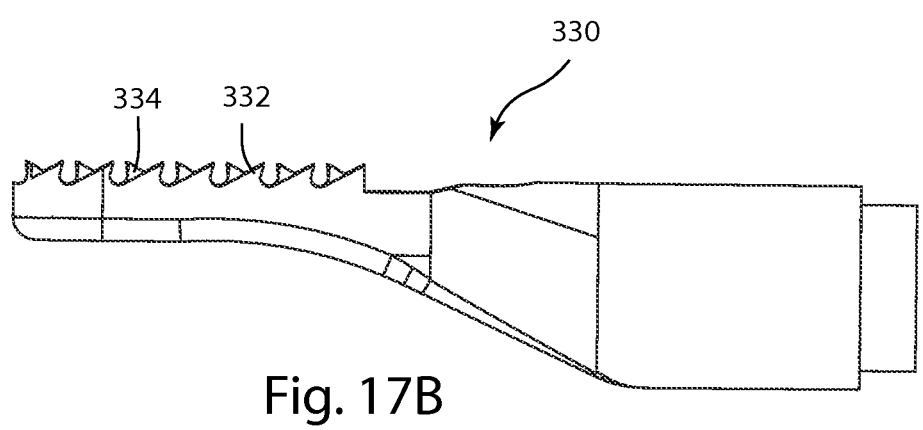
FIG. 17B is a side view of the rasp head of FIG. 17A.

FIGS. 17A and 17B depict a rasp head 340 comprising bi-directional teeth. A plurality of first teeth 332 are oriented proximally, or toward a proximal end 336 of the rasp head, while a plurality of second teeth 334 are oriented distally. When used as part of a reciprocating rasp system such as rasp system 100, tissue cutting may occur in both directions as the rasp head is axially reciprocated.

Figure 18A:
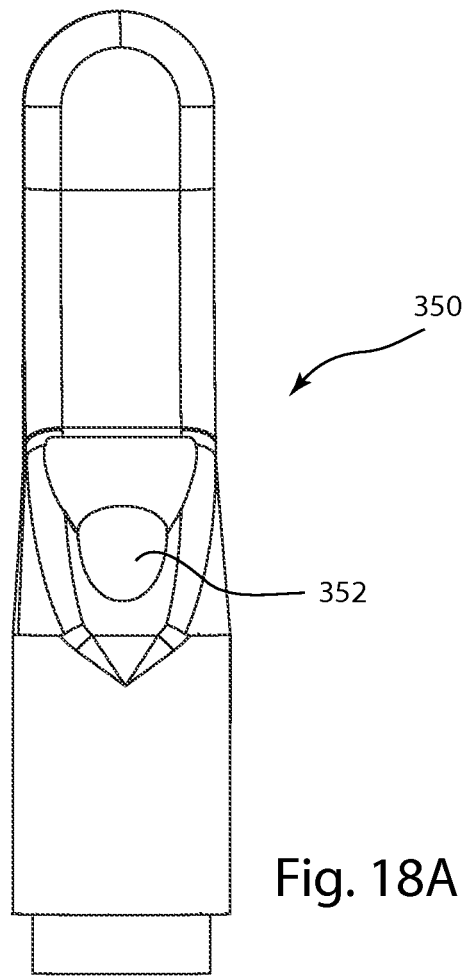
FIG. 18A is an isometric view of an alternate embodiment of a rasp head comprising a suction pathway opening on a back side of the head.
Figure 18B:
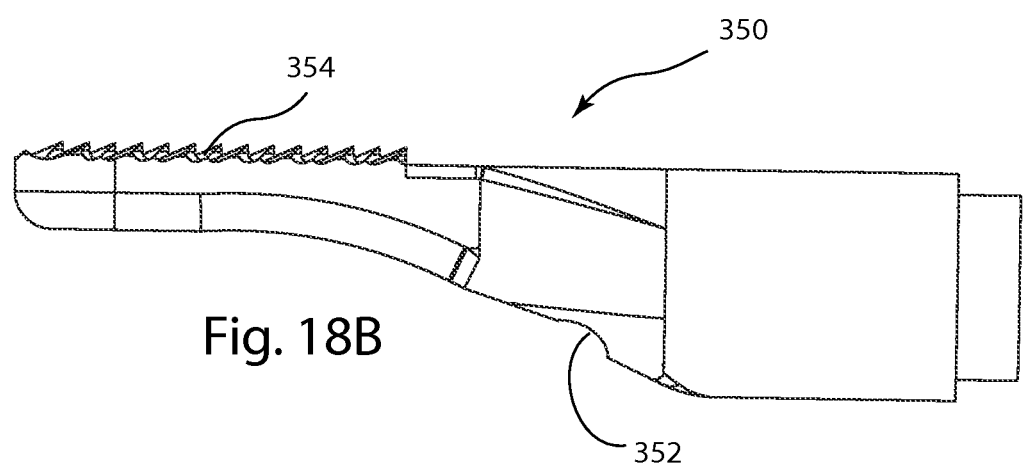
FIG. 18B is a side view of the rasp head of FIG. 18A.

FIGS. 18A and 18B depict a rasp head 350 comprising a suction pathway opening 352 located on the back of the rasp head, on the opposite side as a tissue removal surface 354. It is appreciated that any of the rasp head embodiments disclosed herein may include a similarly located suction pathway opening.

In the embodiments disclosed herein, the rasp head and reciprocating inner shaft may comprise stainless steel, titanium, or other metals or metal alloys. The outer sleeve may comprise metal, plastic, or polymer. The outer housing and rotating hub may each comprise polymer, plastic, metal, metal alloy, ceramic, or a combination thereof. The hub may be coated to improve lubricity or contact strength.

Rasp system 100 may be used in a variety of methods for tissue removal and/or resurfacing. In general, rasp system 100 may be used for abrasionplasty, which encompasses both chondroplasty, or removal of cartilaginous material, and osteoplasty, or removal of bone material. Such tissue removal/resurfacing procedures may be carried out on any bone and/or joint. Similarly, rasp system 100 may be used in treatment of osteochondritis dissecans (OCD) on any affected bone to remove bone fragments. In addition to bone material, rasp system 100 may be used for resurfacing or removal of scar tissue, periosteum, fibrocartilage, functioning cartilage, or nucleus pulposus tissues. Rasp system 100 may also be used in resection and/or resurfacing of bone surfaces in preparation for re-attachment of tendons, preparation for joint fusion, or preparation for implantation of joint replacement device components. The rasp head 108 may be modified to produce alternative embodiments wherein: the size of the rasp head is varied in length, width, and/or thickness; the shape and dimensions of the rasping surface are varied; the number and/or rows of teeth are varied; and/or the orientation of the teeth is varied, among other variations. Rasp 100 and alternative embodiments may be used independently or with common surgical cannulas known in the art. Specific uses for the rasp system 100 and alternative embodiments are set forth herein, however it is appreciated that the rasp may be used in other tissue removal procedures within the scope of the invention.

In the joints of the ankle, rasp system 100 may be used to relieve anterior impingement by removing impinging osteophytes on the talus and/or tibia. Use of rasp system 100 may be advantageous over a burr, as a burr may penetrate too deeply into the bone cortex and cause a fracture in the talar neck. The smaller size and gentler action of rasp system 100 may result in a less aggressive approach than that provided with a burr. Rasp system 100 may also be used in the removal of chondrocytes to address chondromalacia of the talar dome and/or the tibial plafond. Medial and/or lateral guttural impingement of the ankle may be relieved by removal of osteophytes with rasp system 100. Depending on the size, shape and/or accessibility of the tissue to be removed, rasp system 100 comprising rasp head 108 which has a generally flat working surface may be used, or alternative embodiments comprising rasp head 310 with a crescent-shaped working surface or rasp head 280 with a convex working surface may be used.

Rasp system 100 may be used in procedures performed on the knee. Rasp system 100 may be used for symptomatic osteophyte removal, especially along the marginal articular edges of the joint. Rasp system 100 may be used for anterior cruciate ligament (ACL) notch plasty. For this procedure, it may be advantageous to use a system comprising rasp head 310 with a crescent-shaped working surface or rasp head 280 with a convex working surface. Also, a system using rasp head 270 with an angle of 3° to 5° may be ideal for notch plasty access. In addition, rasp system 100 or an alternate embodiment may be used in the knee to perform abrasionplasty to address OCD or chondromalacia.

In the hip, rasp system 100 may be used to address impingement by removal of bony prominences and/or osteophytes. Labral repairs may be performed, such as preparation of the acetabular rim for healing of a labral tear, as a non-limiting example. As in the ankle and knee joints, the rasp may used in the hip for removal of osteophytes and/or chondrocytes to address OCD or chondromalacia. In some procedures in the hip, an alternate embodiment of rasp system 100 comprising a curved shaft portion may be advantageous. In this embodiment the optional outer sleeve may not be required.

In the shoulder, rasp system 100 or alternate embodiments may be used to remove bone and/or cartilage material in at least the following procedures: acromial clavicular joint resection (also known as the Mumford procedure or AC resection); subacromial decompression; glenoid rim abrasionplasty; and osteoplasty in preparation for rotator cuff re-attachment.

In the spine, rasp system 100 may be used in vertebral endplate abrasionplasty, and in preparation for vertebral fusion or artificial disc implantation. Around the facet joints, rasp system 100 may be used for removal of bone spurs, and preparation of articular surfaces for facet joint fusion or replacement. Especially along the curved surfaces around the facet joints, a rasping system comprising the crescent, convex or concave shaped rasp head may be advantageous. Also, the rasp may be used to remove osteophytes or bony prominences in or around the spinal canal.

For procedures in joints of the wrist, a smaller working head surface such as that in rasp head 300 may be advantageous for reaching into confined areas without disturbing adjacent soft tissues. Rasp system 100 may be used for chondroplasty, osteoplasty and other joint preparation procedures in the wrist.

In the elbow, rasp system 100 or alternate embodiments may be used to remove osteophytes on the edges of the trochlea, to prevent impingement on the ulnar nerve. Marginal osteophytes or bony prominences may be removed at the marginal edges of the articulating surfaces of the elbow. For treatment of arthritis, bone spurs may be removed to aid in restoring motion. As with the wrist, use of a system comprising rasp head 300 with a reduced tissue removal surface may be advantageous, as may use of a system comprising a convex or crescent shaped head.

In the skull, rasp system 100 may be employed for sculpting of bony prominences on the cheek areas, forehead, nose, chin and jaw.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A tissue removal device for being driven by a powered rotary handpiece, comprising:
   a rotary hub having a distal end and a proximal end;
   a tissue removal member having a distal end comprising a tissue removal surface and a proximal end, the tissue removal member proximal end coupled in sliding contact with the rotary hub; and
   a motion conversion mechanism comprising a housing, a cam surface and a cam follower surface, wherein the cam follower surface comprises at least one hollow complementarily fitting at least one lobe of the cam surface;
   wherein when the rotary hub is rotated about an axis, the motion conversion mechanism urges motion of the tissue removal member along the axis, wherein the motion consists of reciprocating translation of at least the distal end of the tissue removal member between a first retracted position and a second extended position, wherein in the first extended position the cam follower surface and the cam surface are flush;
   the housing disposed around a portion of the tissue removal member and a portion of the rotary hub, the housing having a proximal end, a distal end and the cam surface facing proximally;
   wherein the rotary hub distal end terminates in a distal end face, the distal end face comprising the cam follower surface;
   the tissue removal member further comprising:
   a shaft key comprising a proximal groove on the outside of a key body, wherein the proximal groove engages a ring for retention within the rotary hub, the shaft key further comprising distal wings configured to fit into recesses of the housing, wherein the distal wings of the shaft key cooperate with the recesses of the housing to prohibit rotary motion of the tissue removal member.

2. The tissue removal device of claim 1, wherein the housing cam surface is distal to the proximal end of the tissue removal member.

3. The tissue removal device of claim 1, wherein the cam surface comprises a first annular surface wherein the at least one lobe comprises at least two identically shaped lobes and the cam follower comprises a second annular surface wherein the at least one hollow comprises two identically shaped hollows, wherein the lobes are evenly interspersed with the hollows.

4. The tissue removal device of claim 1, wherein the tissue removal surface comprises a plurality of teeth, each tooth having a cutting edge, wherein the cutting edges are unidirectionally oriented.

5. The tissue removal device of claim 1, wherein the tissue removal member proximal end is distal to the rotary hub distal end.

6. The tissue removal device of claim 1, further comprising:
   a spring, wherein the spring biases the tissue removal member distally toward the extended position, and wherein the rotary hub urges the tissue removal member proximally toward the retracted position.

7. The tissue removal device of claim 1, wherein the tissue removal member is coaxial with the rotary hub.

8. A tissue removal device for being driven by a powered handpiece, comprising:
   a tissue removal member having a distal end, a proximal end, and a shaft extending therebetween along a longitudinal axis;
   a housing comprising a bore extending longitudinally therethrough;
   a sleeve member having a distal end and a proximal end, the sleeve member fixed to the housing in coaxial alignment with the bore, the tissue removal member extending through the bore and the sleeve member;
   a motion mechanism;
   wherein when the motion mechanism is connected to the powered handpiece, the motion mechanism urges motion of the tissue removal member along the axis, wherein the motion consists of reciprocating translation between a first retracted position and a second extended position along a solitary axis,
   wherein the proximal end of the tissue removal member comprises a shaft key comprising a proximal groove on the outside of a key body, wherein the proximal groove engages a ring for retention within a rotary hub, the shaft key further comprising distal wings configured to fit into recesses of the housing, wherein the distal wings of the shaft key cooperate with the recesses of the housing to prohibit rotary motion of the tissue removal member.

9. The tissue removal device of claim 8, wherein the motion mechanism comprises a drive shaft, the drive shaft coupled directly to the tissue removal member.

10. The tissue removal device of claim 8, wherein the sleeve member is rigid.

11. The tissue removal device of claim 8, wherein the tissue removal member distal end comprises a tissue removal surface having a length extending along the longitudinal axis, and a width transverse to the length, wherein the tissue removal surface is convex across its width.

12. The tissue removal device of claim 11, further comprising:
    a plurality of teeth formed on the tissue removal surface, each tooth having a cutting edge, wherein the cutting edges are unidirectionally oriented.

13. The tissue removal device of claim 11, wherein the tissue removal surface is disposed distal to the distal end of the sleeve member when the tissue removal member is in the first retracted position and when the tissue removal member is in the second extended position.

14. The tissue removal device of claim 8, wherein the motion mechanism comprises a rotary hub having a distal end and a proximal end;
    wherein when the rotary hub is rotated about the axis, the motion mechanism urges the motion of the tissue removal member along the axis, wherein the motion consists of the reciprocating translation between the first retracted position and the second extended position.

* * * * *